United States Patent [19]
Reynolds et al.

[11] Patent Number: 5,911,581
[45] Date of Patent: Jun. 15, 1999

[54] INTERACTIVE COMPUTER PROGRAM FOR MEASURING AND ANALYZING MENTAL ABILITY

[75] Inventors: Josh Reynolds, Laguna Beach; Jeremy Knight, Berkeley, both of Calif.

[73] Assignee: Braintainment Resources, Inc., Laguna Beach, Calif.

[21] Appl. No.: 08/806,500

[22] Filed: Feb. 27, 1997

Related U.S. Application Data

[63] Continuation of application No. 08/391,352, Feb. 21, 1995.

[51] Int. Cl.$^6$ ................................................. G09B 19/00
[52] U.S. Cl. ............................................. 434/236; 434/219
[58] Field of Search ................................... 434/236, 237, 434/219, 220

[56] References Cited

U.S. PATENT DOCUMENTS

| | | | |
|---|---|---|---|
| 3,916,534 | 11/1975 | Riccio | 434/64 |
| 4,057,911 | 11/1977 | Sack | 434/64 |
| 4,058,113 | 11/1977 | Fields | 128/745 |
| 4,770,636 | 9/1988 | Buschke | 434/236 |
| 4,818,234 | 4/1989 | Redington et al. | 434/247 |
| 4,934,386 | 6/1990 | Walker et al. | 131/329 |
| 4,974,833 | 12/1990 | Hartman et al. | 482/3 |
| 5,017,142 | 5/1991 | Bemis et al. | 434/220 |
| 5,079,726 | 1/1992 | Keller | 364/551.01 |
| 5,230,629 | 7/1993 | Buschke | 434/236 |
| 5,344,324 | 9/1994 | O'Donnell et al. | 434/258 |
| 5,447,166 | 9/1995 | Gevins | 128/731 |
| 5,595,488 | 1/1997 | Gozlan et al. | 434/236 |

*Primary Examiner*—Robert A. Hafer
*Assistant Examiner*—John Edmund Rovnak
*Attorney, Agent, or Firm*—Penman & Collins

[57] ABSTRACT

An interactive automatic system and technique for measuring and training of mental ability. In the illustrative embodiment, the invention is implemented on a computer which automatically presents a variety of visual and auditory stimuli. The system then measures reaction to the stimuli, adjusts certain stimulus parameters, and provides scores in response thereto. The scores are tabulated and displayed for analysis. In particular embodiments, the invention tests for physical reaction time, perceptual awareness thresholds, attention level, speed, efficiency and capacity of information processing by the brain and elementary cognitive processes, including memory, memory access and decision-making speed. The invention measures, identifies and quantifies noise in the subject's brain and elementary cognitive processing system, and the information exchange rate between the subject's left and right brain hemispheres. The inventive system compiles a history of the test scores, renders an overall performance rating, and delivers comments based on the subject scores. The complexity of the tests are adjusted based on the scores to optimally challenge cognitive capacities, thereby rendering more accurate evaluations of cognitive capacity, and optimizing learning of desired improvements in perceptual, physical and mental response speeds and efficiencies.

25 Claims, 14 Drawing Sheets

FIG. 2
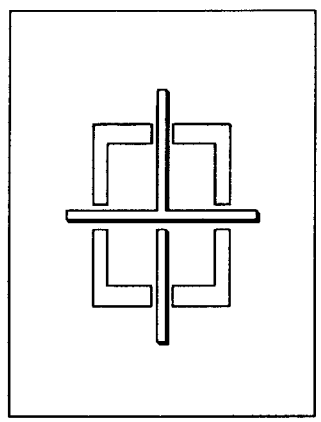
FIG. 11(a)
SNJ
FIG. 11(b)
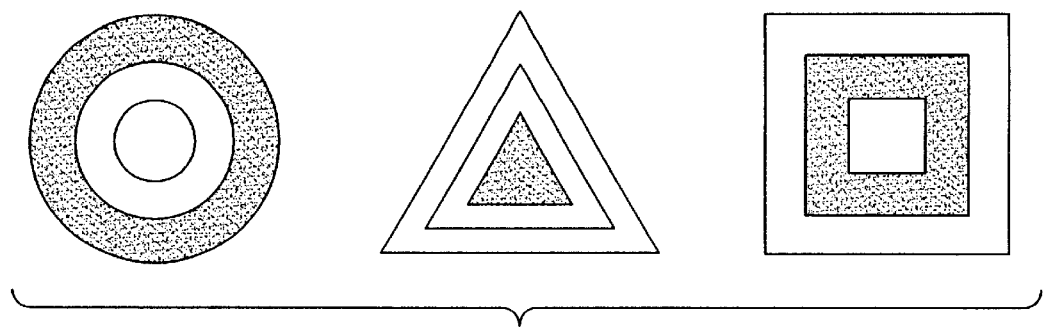

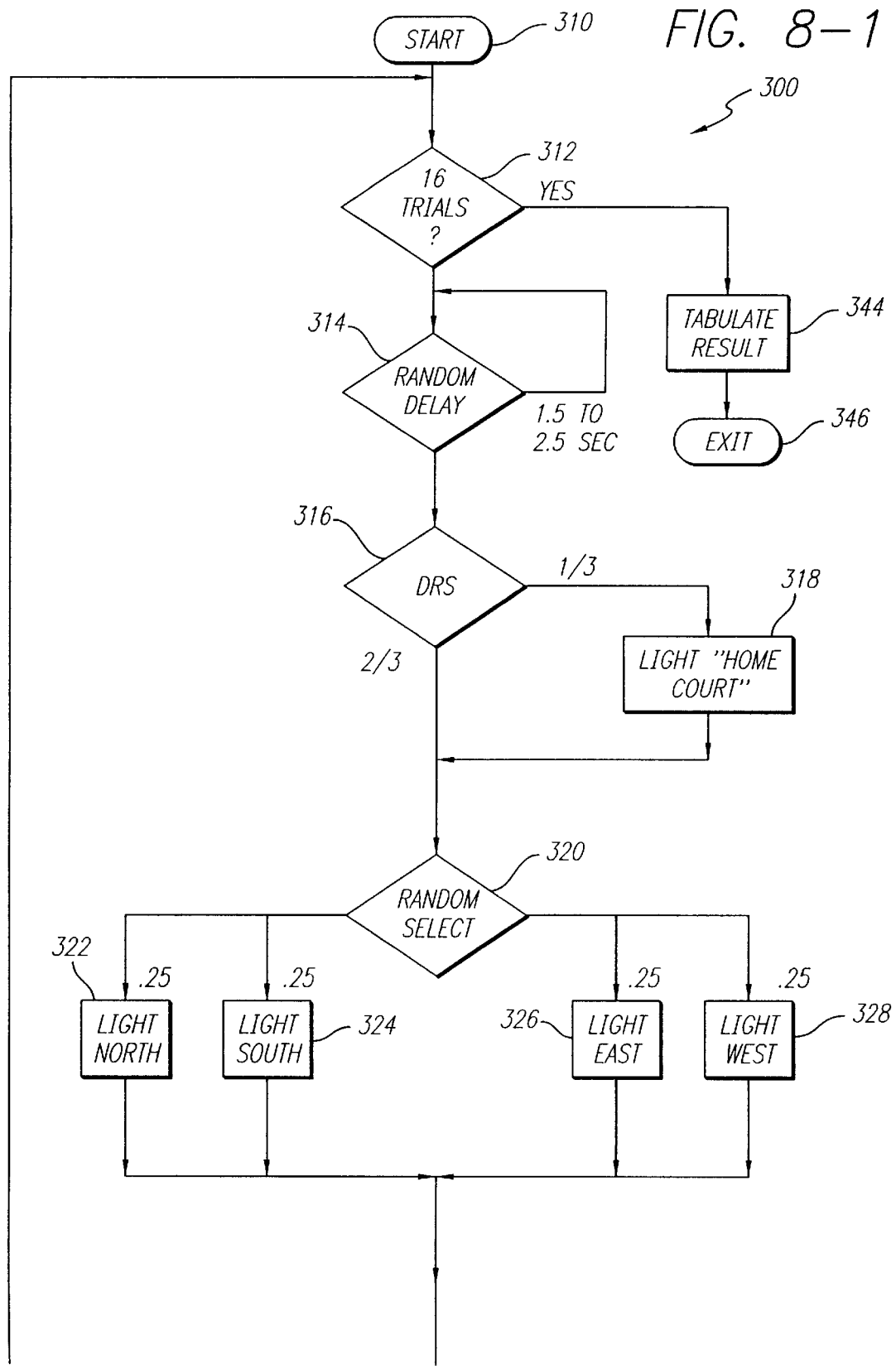

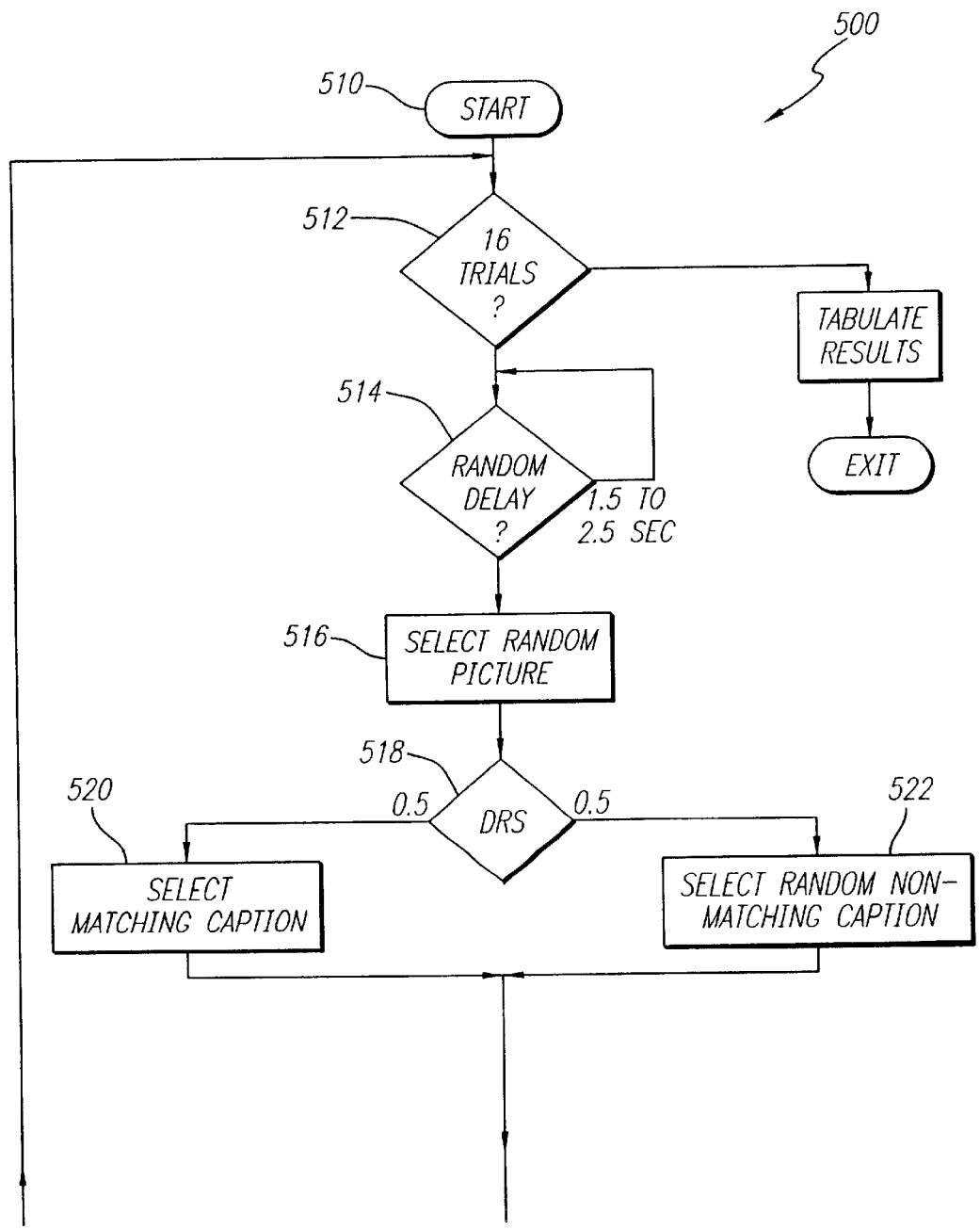

INTERACTIVE COMPUTER PROGRAM FOR MEASURING AND ANALYZING MENTAL ABILITY

This is a Continuation of Application, Ser. No. 08/391,352, filed Apr. 12, 1996.

BACKGROUND OF THE INVENTION

1. Field of the Invention

The present invention relates to 0 computer based testing systems. More specifically, the invention relates to systems and methods for measuring, analyzing and training improvements in mental ability.

2. Description of the Related Art

Scientists and psychologists have long sought an objective measure of general mental ability that is independent of cultural bias (acculturation). Most pen and pencil PSYCHOMETRIC ("IQ") tests (e.g., Stanford Binet and Wechsler) are biased to the degree that their questions favor prior learning of: procedural skills (e.g., use of math tables enabling faster solutions), strategies (e.g., how to solve certain problems), and language (e.g., alphabet, vocabulary, colloquialisms).

Although IQ tests purport to measure native mental aptitude, or ability, per se, a growing percentage of educational and cognitive psychologists have argued that, "individual differences in tested IQ are attributable to differences in the opportunities afforded by the environment for acquiring the specific skills that are called for by the standardized tests of intelligence".

In an attempt to identify a common factor that accounts for individual variations across a broad range of mental tests, scientists have constructed the term 'g'. The degree to which any test reflects native intelligence, or mental processing skills, versus acculturated learning, is its g-factor, or g-correlation.

A 'g-factor' score results from a factor analysis of a wide range of mental ability tests, and relates to those components of the tests that are most highly correlated in their predictability of test results. However, although g is often used as a synonym for IQ, in fact, it is not a measure of any kind of knowledge or mental skill. That is, g is not related to cognitive content g reflects cognitive capacity, that is, information processing capacities (speed, capacity and efficiency). The knowledge and skill content of performance on mental ability tests is merely an expression of g which reflects the overall capacity of information processes by which knowledge and skills can be learned and effectively applied, such as, in an IQ test.

Over the past 20–30 years Cognitive Science has developed the theory that cognitive ability, i.e., g, is based on the brain's (information processing) speed. Studies have revealed high correlations between highly g-loaded mental tests (e.g, Wonderlic, Ravens and WAIS), and brain-speed, as measured via neural conduction velocity (optic-nerve transmission speed), and chronometric (reaction speed) cognitive tests, for instance.

Underlying g, or basic intelligence, are elementary cognitive processes (ECPs) involved in every stage of cognition from perception to decision-making. More specifically, ECPs are comprised of the following components: the perceptual registration ("apprehension") of the stimuli (bits of information); the identification ("discrimination") of the information; the "selection" and "encoding" of the information, and the appropriate reaction, be it: physical (sensory-motor), i.e., "simple" reaction-time (RT), or; cognitive, ie, "choice", "discrimination" and "decision" RTs. Cognitive reactions involve the additional ECPs of; "rehearsal" and further "encoding" of appropriately selected information while, short and long term memory files are simultaneously accessed, followed by the "transformation" and "manipulation" of retrieved information for the purposes of making the appropriate choice, discrimination or decision response. Any test that challenges and quantifies elementary cognitive processes is referred to as an elementary cognitive task (ECT).

A simple reaction-time (RT) test involves a single (sensory-motor) response when a certain event happens, such as, pressing a button when a light goes on. A choice RT test involves two or more possible choice responses. For example, "If a red light flashes on the screen, press the R key, and if a green light presents itself, press the G key." A discrimination RT test generally involves the use of short term memory to render a yes/no response. As an example, a string of letters is presented for quick review, quickly followed by a second set of letters, with the requirement that the subject determines whether any letter in the second group was in the first group and respond as quickly as possible.

And, a decision RT test requires the access of short term memory and/or long term memory (LTM) in order to render the correct "split-second" decision. For example, the stimulus may pair a word with a picture on the computer. The Rule might be, "If the word and picture are the same, press the right arrow key, otherwise press the left."

Although "simple," RTs show a relatively low correlation to IQ, choice (and especially) discrimination and decision RTs demonstrate a relatively high (over 50) correlation. In addition, the higher the number of alternative choices, or possible responses, the higher the test's g-factor. A primary indicator of the g-value of an ECT is the length of time required for a correct response. For instance, simple RTs are typically 275 milliseconds (ms). However, choice RT increases as a log function (to the base 2) of the number of choices (Hick's Law). Typically a four choice test might require 350 to 400 ms. In a decision speed test with a random rule-changing cue, response times typically exceed 1000 ms. RT times around 1000 ms indicate the full engagement of "Working memory" and are considered to be highly g-loaded. However, RTs much over 1000 ms typically reflect non-elementary (meta) cognitive processes, such as, 'thinking' (computations based on learned strategies or procedures, generalizations, etc.).

The functional processing-system serving the elementary cognitive processes is what Cognitive Science terms "Working memory". It is likened to a computer's central processor. The faster the processor, the smarter the computer and brain.

The ideal mental ability test, therefore, would quantify as many ECPs as possible, that is from perception and simple RT, to choice and decision RT.

In response to the need to eliminate cultural bias from the quantification of g a number of electronic and chronometric methodologies have been employed revealing various physiological signatures (electrical, chemical and metabolic) and information-processing capacities of the brain showing high correlations with g.

Various test measurements revealing significant correlations with g include: cognitive chronometric (RT) tests including "Choice RT" and "Discrimination (decision) RT"; "neural conduction velocity"; brain (wave) evoked potentials; brain hemisphere coherence (integration, or synchronicity); total synchronous (alpha and theta) brain wave "energy-under-the-curve"; and others. However, none have shown the practicality, ease of administration and fundamental potential as the chronometric cognitive (RT) tests.

Over 130 years ago Sir Francis Galton advanced the notion that "reaction speed" reflected general intelligence. One-hundred years ago American psychologist J. Allen Gilbert at Yale University was first to demonstrate a relationship between RT and intelligence. RT IQ correlation studies continued over the years. The modern era of choice RT chronometric intelligence tests started around 1952 when W. G. Hicks discovered that, multiple "choice" reaction times increase as a linear function of the increase in the amount of information presented to the subject, when information is measured in binary bits, that is, the logarithm (to the base 2) of the number of choices. This relationship has become known as Hick's Law.

In 1964, E. Roth, using choice RT tests, found that individual differences in the slope of RT as a function of bits (i.e., the rate of information processing), are correlated with IQ. This was one of the first demonstrations of a relationship between (cognitive) response speed and intelligence as predicted by the general theory that, IQ tests measure, among other things, the degree of learning that results from one's information processing capacity.

More recently, Steinburg, Nettlebeck and Jensen, working independently, have measured a number of assumed different ECPs (e.g., inspection time and dual discrimination RT) discovering that, the greater the number of different ECP components measured, the higher their collective g-correlation.

To date most, if not all, chronometric research has been experimental rather than application oriented. In order to render the field viable as a mass population measurement system, the following are (minimally) needed: (1) a comprehensive battery of ECTs that quantify most, if not all, of the known elementary cognitive processes, components and mechanisms of cognition, including; perceptual awareness, brain processing speed, cognitive processing (choice and decision) speeds, working memory capacity, and speed of long term memory (LTM) access (from episodic, semantic and/or symbolic divisions of LTM), and the subsequent speed and efficiency of working memory's organization of relevant data to make a correct choice or decision; (2) a comprehensive battery of ECTs that are truly interactive, whereby test complexity (difficulty) is adjusted on-line, depending upon the speed, accuracy and consistency (efficiency) of the user's responses, in order that the task can optimally challenge, or "load", user's ECP (or, working memory) capacity to its maximum potential, and; (3) an automated computer program (or otherwise electronic device) incorporating such a battery of ECTs that can easily be run on almost any contemporary computer hardware.

It should also be noted that the refined quantification of cognitive components that make up a more generalized mental ability might be helpful in aiding educators and employers to better qualify and place individuals, as well as address their individual cognitive strengths and weaknesses.

In the final analysis there appears to be a real and timely need for a practical yet fair way to quantify intelligence, or g, and its sub-components, whose test results reflect those cognitive processing capabilites underlying "intelligence", and which are not influenced by one's cultural advantages or disadvantages, or even by one's genetic history which may have predisposed the nature of one's 'intelligence' to be different than the qualities of intelligence deemed to be most appropriate for measurement by tests developed some 25 to 50 years ago.

SUMMARY OF THE INVENTION

The need in the art is addressed by the present invention, which, in a most general sense, provides an interactive automatic system and technique for measuring and analyzing mental ability. In the illustrative embodiment, the invention is implemented on a computer which automatically presents a variety of visual and auditory stimuli. The system measures reactions (or lack of) to the stimuli, and provides immediate on-line feedback of results, while interactively adjusting test complexity to optimally challenge the cognitive capacity being measured. The system renders a number of useful measurements, based on proprietary manipulation and analysis of continuous data generated. Appropriate and meaningful cognitive scores are then tabulated, and displayed for analysis.

In particular embodiments, the invention tests for: physical reaction time; perceptual awareness thresholds; brain-speed, and; the speed, efficiency and capacity of elementary cognitive processes, including choice, discrimination and decision responses, memory-access and information-retrieval. The invention also quantifies the subject's degree of focus or attention and working memory's speed of accessing long term memory files believed to reside in both left and right brain hemispheres.

In addition, the complexity of the tests are adjusted on-line, based on individual test results, in order to optimize learning of desired improvements in awareness, attention and in speed and efficiency of brain and cognitive processes. The inventive system also compiles a historical comparison and analysis of the test scores, presents written comments, and provides a performance rating system all graphically displayed.

BRIEF DESCRIPTION OF THE DRAWINGS

FIG. 11(a) and (b) depict display figures utilized by the short term memory test.

DESCRIPTION OF THE INVENTION

Figure 1:
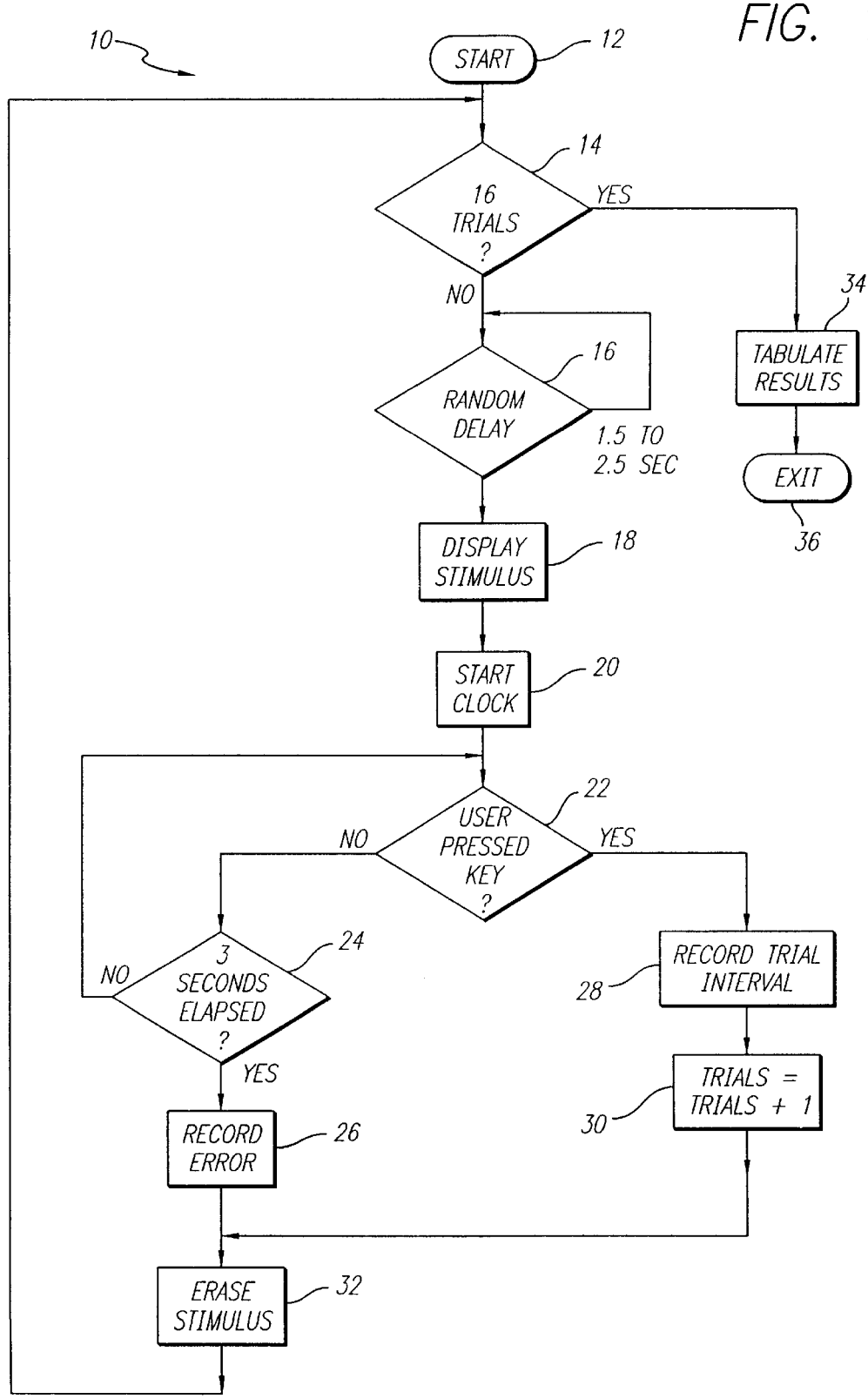
FIG. 1 is a flow diagram of a routine which administers a reaction time test in accordance with the teachings of the present invention.

Illustrative embodiments and exemplary applications will now be described with reference to the accompanying drawings to disclose the advantageous teachings of the present invention.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

There is a growing consensus that elementary cognitive (information) processes, rather than learned cognitive content and skills, most fairly reflect native intelligence, or g. It has been relatively well established that information processing capacities accurately reflect real mental ability, and that info-processing test scores, such as, choice reaction-times, demonstrate high correlations with g. Furthermore, it has been clearly demonstrated that such information-processing capacities, or ECPs, can most easily, comprehensively and accurately be measured via the use of elementary cognitive chronometric tasks. And, furthermore, resultant RT test scores have been highly correlated to mental ability tests, especially those tests, such as, Wonderlic, Ravens, et al, that have a particularly high g-loading.

In other words, it appears that the measurement and evaluation of elementary cognitive processes, which influence, if not enable and determine, learning, and which underly the cognitive expressions of intelligence, might render a more accurate and comprehensive analysis of raw mental ability. An analogy might serve here. Intelligence is an expression of the power of the underlying "muscle" of the brain. Physical strength is the expression of the power of the underlying physical muscles. To most accurately measure the power of a muscle, one would use a weighted, or otherwise resistively loaded, system offering up the maximum load that the muscle can move or lift. To measure the muscle's strength by (indirectly) testing the person's ability to heave a 16 lb. shot, for example, would be relatively inaccurate, since other factors, such as learned technique, practice, etc., also determine how far one could "put the shot".

Likewise, an IQ test could be likened to a track meet for the mind. The IQ test score reflects factors other than merely brainpower. Therefore, a more accurate reflection of mental ability might be derived by directly measuring the brain's power output, that is, its computational speed and efficiency.

It has been demonstrated that the elementary cognitive tasks (ECTs) which produce the highest g-correlated results are comprised of a battery of tests with: each evaluating a different elementary cognitive process (ECP); the battery measuring as many ECPs as possible, and; one or more tasks evaluating as long a chain of ECPs as possible. For instance, this might be a single test that measures perceptual thresholds, brain-speed, choice and decision speeds and efficiencies, short-term "working" memory, long-term memory access speed/efficiency, simultaneously.

It is most likely that adding interactivity to such a battery of ECTs can further enhance the test's g-factor, since the true potential of any elementary cognitive capacity can only be revealed if it's fully challenged.

To evaluate the full capacity of any ECP, the test must fully load working memory. WM is the operational component of short-term memory. It is likened to a computer's central processor.

Working memory (WM) serves each of the elementary cognitive processes. Loading WM requires (interactive) response-based adjustment of test complexity to fully tax WM capacity to its limits (in processing speed, efficiency and memory capacity). For instance, WM has a relatively limited channel capacity. It can only efficiently process one task at a time. WM "capacity" is defined in terms of: its optimal processing speed (including memory retrieval); its processing efficiency (accuracy and consistency), and; its processing capacity ("memory", or amount of information it can successfully handle at one time).

Interactive ECT complexity-adjustment, random stimulus presentation, uncertainty of stimulus type, random rule changes, psychological pressure for speed without errors (performance), positive and negative reinforcement of performance, psychological status for achievement, are all relevant factors that optimize WM loading, thus reflective of true cognitive ability.

Likewise, the above factors also enhance the possibility of cognitive-capacity enhancement learning, especially if the user being tested is also provided individual trial-event feedback of results. Another example might serve here. Imagine trying to improve your game of darts blind-folded. Even if a friend reported where each dart landed, the lack of immediate, on-line, direct feedback makes improvement considerably more difficult.

Therefore, the key to learned cognitive enhancement is based on: the immediate, direct, on-line feedback of appropriate result variables; the interactive adjustment of task dificulty so that the brain-cognitive system's main machine, Working memory, can be fully challenged (imagine trying to build muscle-power with a weight that can be easily lifted), and; challenging all of the brain's various elementary cognitive processes and their capacities.

Finally, it would seem that chronometric reaction-time computer programs might offer a most desirable, non-invasive and practical way to test, quantify and train elementary cognitive processes, or mental ability.

Although, historically, chronometric cognitive tests have demonstrated promising potential in experimental research environments, they have had limited market appeal and application potential for a number of reasons, primarily: (1) their lack of interactivity, (2) lack of comprehensiveness (a complete ECT battery is significantly more effective and engaging), (3) their inability to work with previous hardware (it has only been within the past few years that computer processor speed, and screen refresh-rates, have been adequate for the testing of perceptual and mental reaction-speeds down in the low millesecond range).

In addition to the quick and equitable quantification of cognitive capacities known to underly intelligence, another valuable application of the invention would be the qualification of conditions such as sleep, alcohol, nutrition and drugs for their affect on mental/cognitive capacities. Simple reaction-time and dexterity tests, brain wave pattern analysis, bio-chemical analysis, subjective experience evaluation, behavioral pattern observations, and other measures have historically been used in an attempt to accurately quantify and qualify mental and physical performance altering "conditions".

Unfortunately, conventional methods typically produce relatively gross analysis, especially regarding qualitative factors. For example, the accuracy of blood alcohol analysis as a measure of one's true condition is questionable with respect to an individual's actual reflexes, awareness level, etc.

In another example, scientists currently researching the mental performance boosting affects of vitamins, herbs and pharmaceuticals, such as the new class of nootropic drugs, have no highly accurate, reliable and comprehensive way to measure the drug's true impact on elementary cognition, and its components. And, although memory recall and other conventional aptitude tests have been used with limited success, their primary limitation is the limited number of times they can be used in a relatively short time frame. Furthermore, these tests are significantly restricted in the number of different cognitive processes they can measure.

One of the most desirable cognitive components to measure in the quantification of mental ability, is brain-cognitive efficiency. Recent use of PET scans (Haier, UC Irvine, Calif.), has demonstrated reduced brain metabolic rates with more intelligent people. That is to say, a smart person uses less of their brain, more efficiently, than a less smart person when engaged in some cognitive task. Efficiency is the relative ease, consistency and accuracy in performing a mentally challenging task. A direct, non-invasive system for the measurement of brain-cognitive efficiency might offer significant potential for the qualification of mental preparedness for, for example, pilots, air traffic controllers, athletes, soldiers going into combat, executives going into major negotiations, etc. Or, the affects of drugs, alcohol, etc. might best be qualified via brain-cognitive efficiency testing.

At the heart of the present invention is a unique means for the evaluation of brain-cognitive efficiency, in terms of response consistency and accuracy. This is accomplished by rendering a measurement of appropriate errors and individual intra-test variabilites rendering a standard deviation of appropriate scores. By combining the standard deviation, speed and accuracy of responses the program renders a highly revealing and meaningful efficiency score.

ECTs are "tests" that quantify ECPs by specifically targeting working memory only (vs. meta-cognitive mechanisms, eg, learned skills, strategies, etc.). The most representative ECTs are chronometric tests which quantify information-processing speed, capacity (memory in number of information bits), and efficiency (consistency and accuracy). The most comprehensive measure of g is via a battery of ECTs which measure as many individual ECPs as possible, minimally: perception thresholds; brain-speed; WM capacity; WM processing speed (eg, data "rehearsal", "encoding" and "manipulation"); WM speed of accessing both short-term memory and several "areas" of long term memory (episodic, semantic and symbolic), and; WM efficiency.

It is not known whether the sum of the scores of many individual ECPs (eg, the above) has a higher correlation with g, than a single task which engages a longer string of cognitive processes. However, the combination of the two, that is, summing the individual ECP scores with the "long ECP chain" score undoubtedly creates the highest g-correlation, especially when the tasks also; 2) "load", or challenge, WM to the threshold of breakdown (overload). This is accomplished by (interactively) adjusting the test complexity until the pre-breakdown thresholds are reached.

At this point WM capacity has been fully loaded, or challenged. The ability to interactively load (increase) test complexity on-line while a subject plays the game, for example, is very important in order to most accurately accurately determine peak threshold (ECP) capacity, as well as to optimize development of such capacity.

The invention represents an automatic-and-interactive program, for computers or adapted electronic device, that tests, analyzes, and potentially improves, how the subject perceives, thinks and reacts, physically and mentally. The program is designed to convert any computer into an interactive test and training system.

With frequent use, or training, the program expands the subject's awareness of how he or she perceives, thinks and reacts, potentially training the user, via brain biofeedback, to improve his or her powers of awareness, focus, mental quickness, clarity and efficiency, memory retrieval speed, capacity and choice-decision speed.

The program also plots performance scores over daily, weekly and quarterly periods. It allows the subject to register comments, such as any unusual conditions surrounding any test. In this way, one learns about the (mental and physical) performance effects of drugs, emotions, drinks, foods, vitamins, sleep, exercise programs, and etc. The program also challenges the subject to improve upon his "baseline" score using on-line feedback display of comparative results with positive, and where appropriate negative, reinforcement of responses, along with interactive adjustment of test complexity (difficulty) to most fully challenge the brain and mind and optimize cognitive-enhancement potential.

In addition, the program provides comments after the entire test battery is completed yielding test interpretations, as well as insights into, and appropriate suggestions.

The program's biofeedback capacity trains the above brain-cognitive capacities by "shaping responses" towards improvement in perceptual, data-processing and decision making abilities, as desired. The program also detects the level of noise in the brain's cognitive processing pathways (neural noise) which is highly correlated with mental ability and stress, and is believed to reflect emotional levels of anxiety and frustration.

By uniquely weighing and valuing a host of test parameters, the following examples of individual and complex adjusted scores are rendered:

physical (sensory-motor) reaction time
    perceptual thresholds
    brain speed and efficiency
    information processing speed and efficiency
    neural noise
    attention level
    choice reaction speed and efficiency
    decision (discrimination) reaction speed and efficiency
    long term memory access speed
    short term "working" memory capacity
    information exchange rate between the brain hemispheres
    a physical performance potential rating
    a mental performance potential rating In short, the program measures, evaluates and trains perceptual, information processing and mental reaction-speed capacities believed to underly the elementary cognitive faculties of awareness, physical reflexes and intelligence.

Yet another, and perhaps less obvious, application of the technology is to add true interactivity to multi-media CD ROM entertainment, edutainment and education software. The field of interactive software is experiencing a dynamic growth phase with the advent of new multi-media mediums, such as, CD ROMs, etc.

Interactive is a term commonly used describing the ability of the user to edit or otherwise influence the content and it's delivery via the software-hardware system, such as, a floppy disc or CD ROM and a computer. However, such interactive systems have no way of knowing how such new content affected the user.

The technology enables a relatively new and improved form of interactivity, wherein the content is actually shaped by the user's mental and physiologic states (as evidenced by their reactions), which new content, in turn influences the user (and their cognitive state), etc.

For instance, an interactive loop would be formed by using an EEG to monitor viewer brain wave patterns evidencing the degree of attention payed to (or interest in) a CD ROM story (media content) displayed on a screen. If the content, or "presentation stimuli", were qualitatively adjusted by the user's brain waves so as to shape a desirable brain wave state (reflecting one's paying more attention), such interactive shaping of content presentation by user psycho-physiologic, or cognitive, states could be called interactive.

Within the entertainment and edutainment fields there is a growing demand for "interactive" software and CD ROM applications which teach while they entertain, or otherwise, engage. For instance, computer software developers have added "interactive" tutorial texts to their programs for the purpose of accelerating the learning process as well as making it more user friendly. However, although most if not all of such programs address cognitive content-enhancement, that is, the learning of new information and skills, such as, how to use Windows, or fix your Volkswagon, few if any address cognitive capacity-enhancement, that is, training improvements in such cognitive capacities as, memory, attention span, decision speed, etc.

Cognitive capacity-enhancement training requires on-line and immediate measurement, analysis and feedback of user's cognitive states (eg, attention, memory capacity, mental reaction speed, etc.) which interactively adjust content, or "stimulus presentation". For instance, if such a training program were to test and train one's perceptual threshold (or, "seeing speed"), the program would need to be able to interactively adjust the "presentation time" of the "stimulus" until it determined the user's perceptual threshold, based on their responses.

It's obvious how this interactive loop between the hardware/software system and the user (ie, their responses which reflect some underlying cognitive state, or capacity, such as mental reaction speed) is necessary for the accurate evaluation of certain cognitive ability. However, it's equally important that on-line and immediate feedback be provided to the user for optimal learning of trained improvements in any cognitive capacity.

Inspite of the demonstrated market interest in self-improvement products, such as, books, self-help seminars, etc., there has been a relative dearth of software products addressing cognitive- capacity enhancement. One primary reason for this has been the lack of user-friendly (eg, non-invasive vs. electrodes attached to the brain) true "inter-activity".

It would seem to be of significant advantage, therefore, to the mass marketability of such cognitive capacity testing and training programs and systems to have user-friendly true (bio) interactivity between the user's cognitive states (such as, the measured responses indicating perceptual thresholds), and appropriately adjusted content presentation (and feedback display).

The present invention teaches a new, non-invasive and computerized methodology for the testing and training of cognitive capacities, and, perhaps most uniquely, is so designed to enable a number of new and useful broad market applications of interactive educational and entertainment software, from standard floopy disc software programs to multi-media CD ROM.

For instance, the present invention allows for the unique value-added improvement of standard interactive CD ROM technology and systems, converting them into an interactive testing and training, as well as entertaining, system products. This could open up whole new markets beyond edutainment, such as, braintainment, for example.

As an example, imagine an exciting kid's game which challenged most if not all of their cognitive capacities and brain processing pathways. For instance, the game could present shape-shifting Friend and Foe characters, unexpectedly and at near subliminal threshold speeds. Speed of advancement in the game depends on the player's (very) quick recognition of, and appropriate responses to, his Friends and Foes. Not seeing a Foe, or misidentifying a Friend, or seeing a pack of Foes too slow (late), would all set you back in the game. Conversely, the quicker you could see (your perceptual threshold), and identify and appropriately respond to (making a correct choice and decision) Friends and Foes, the faster or farther you'd advance and perform. With interactive response, the characters would learn how the subject is seeing, thinking and reacting. The "monsters" on the screen would start to outsmart the user.

While playing this game the player's cognitive capacities of perception, physical and mental reaction and discrimination capacities (speed, capacity, efficiency), short term memory recall, long term memory-recall speed, and most importantly, attention levels, are all being quantified, analyzed and, optionally, displayed for review.

While the child is having fun, and tuning up his brain, his parents or educators are analyzing his mental performance capacities. They will also discover how dull or sharp he is today. This will not only reflect how well he might learn or test today at school, but over time correlations will be revealed between their child's (junk food vs. healthy) eating habits, exercise program, nutritional supplements, emotional stress, etc., and his mental and physical performance.

Another envisioned application of such An interactive floppy or ROM disc program might be for seniors. It is known, for example, that cognitive abilities normally start to decline after years 65 (statistically). That is, unless the brain can be exercised in the appropriate manner. Interactive brain-games could be employed to slow down, stop, if not reverse, at least for a temporary time period, this cognitive degeneration.

REACTION TIME TEST

FIG. 1 is a flow diagram of a routine which administers a reaction time test in accordance with the teachings of the present invention. During this test, the system (computer) displays a figure such as that shown in FIG. 2 and measures the time required for a subject to depress a key. A random delay is introduced at step 16 before the figure is shown, so that the subject cannot predict from past experience precisely when the test figure will appear (a similar random delay is used in the other tests). The reaction time for each trial is recorded. The statistical analysis performed on the reaction time data for this and the other tests is described below, under DATA ANALYSIS. FIG. 2 is a test figure such as that utilized by the system of the present invention for testing reaction time.

SUBLIMINAL AWARENESS THRESHOLD TEST

Figure 3A:
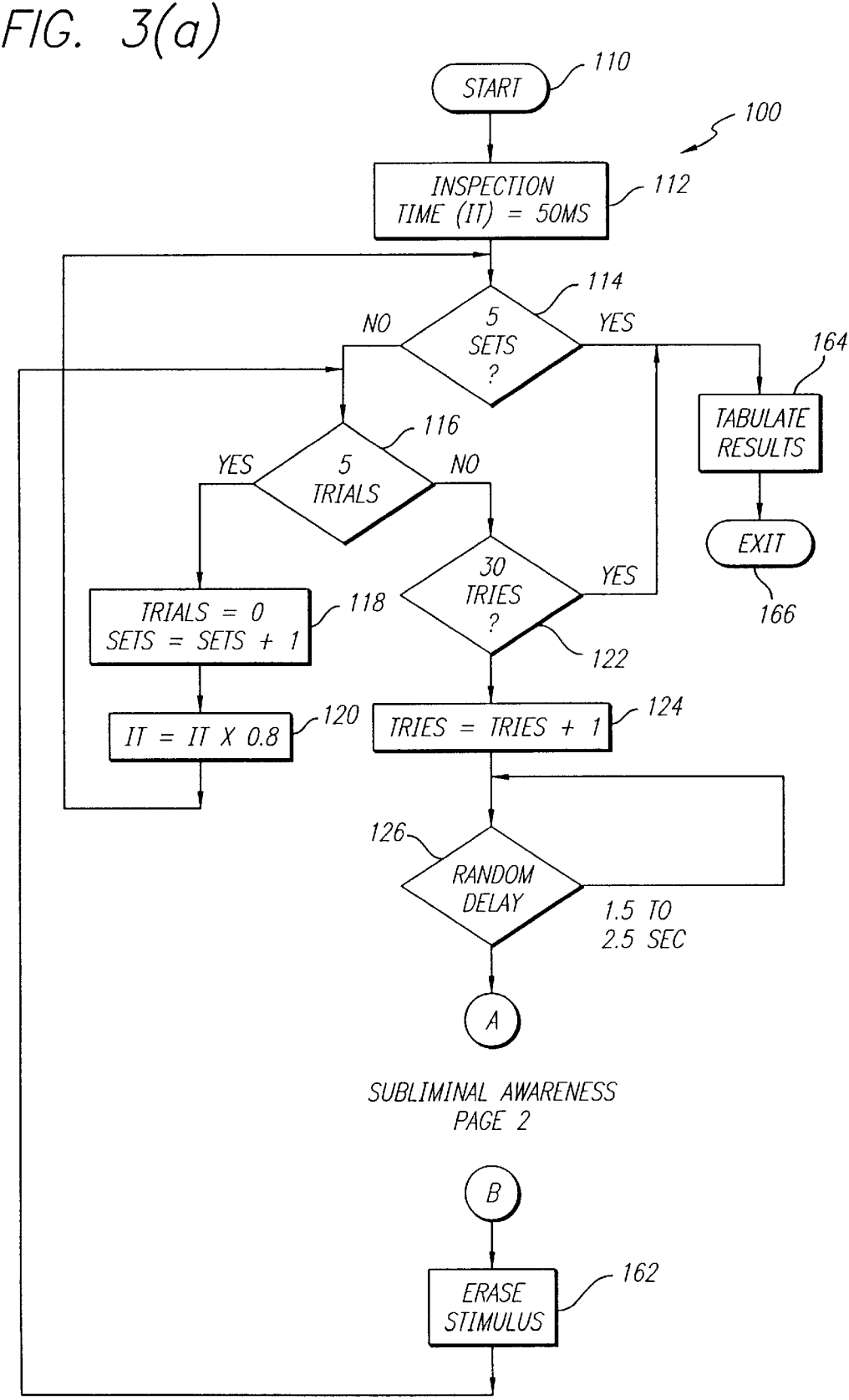
FIGS. 3(a) and 3(b) depict a flow diagram of a routine which administers a subliminal awareness threshold test in accordance with the teachings of the present invention.
Figure 3B:
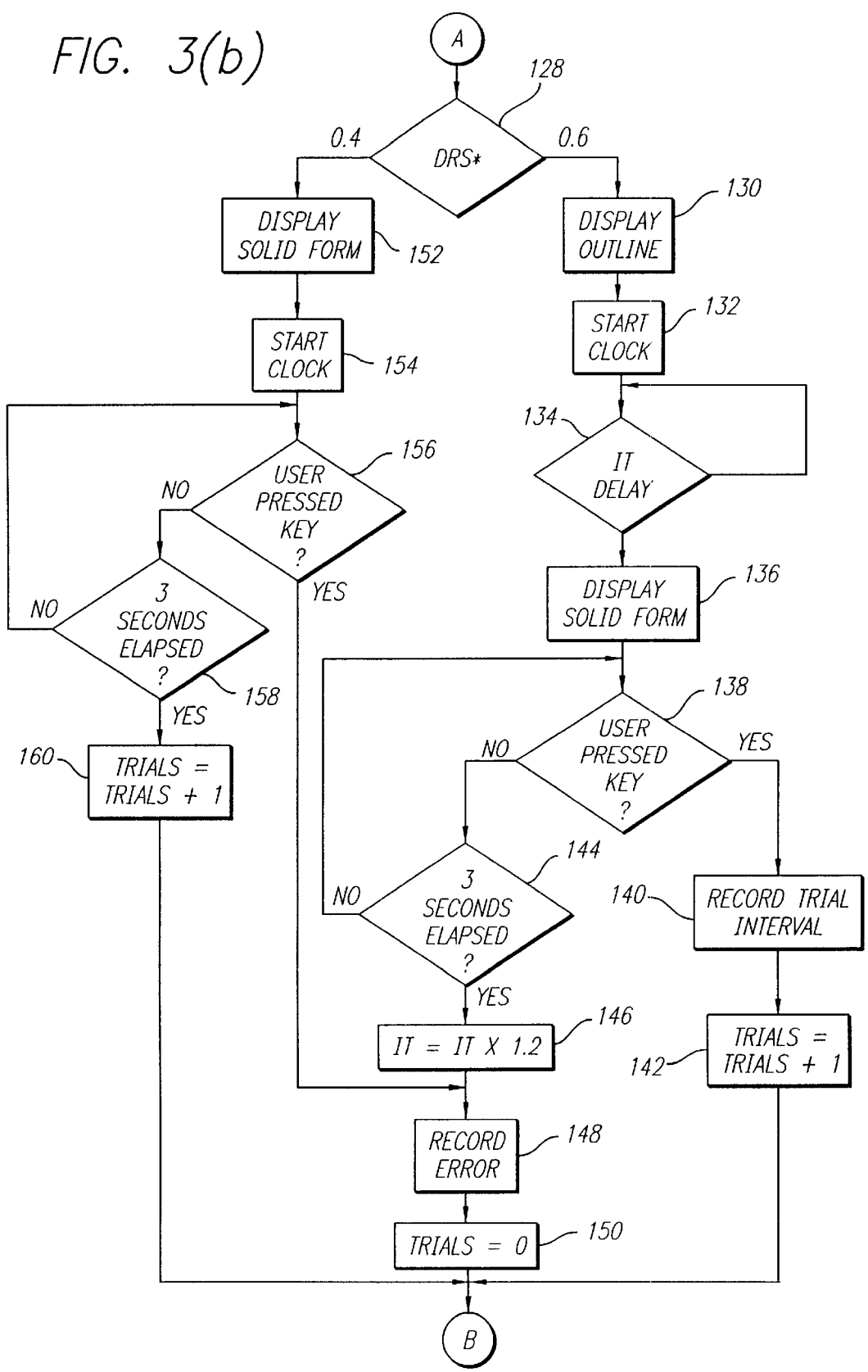

FIGS. 3(a) and 3(b) depict a flow diagram of a routine which administers a subliminal awareness threshold test in accordance with the teachings of the present invention. This test measures the limits or threshold of one's ability to perceive a very brief stimulus. The subject is presented with one or two possible stimuli: a very brief outline of a 4-pointed star immediately turning into a solid star, or a solid star only.

Figure 4A:
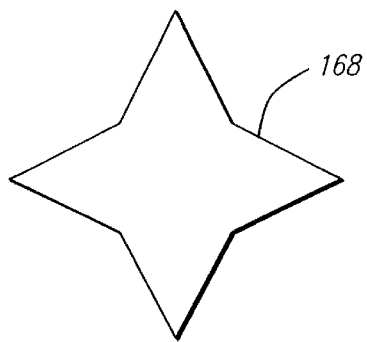
FIGS. 4a and 4b depict a figure useful in the administration of the subliminal awareness threshold test in accordance with the present teachings.
Figure 4B:
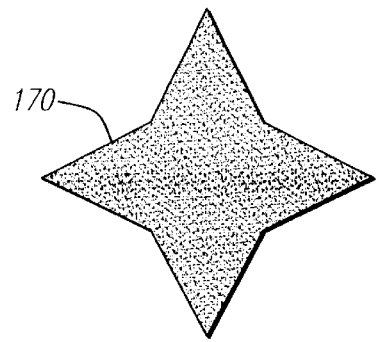

FIGS. 4(a) and 4(b) depict a figure useful in the administration of the subliminal awareness threshold test in accordance with the present teachings. The objective is to discriminate between the two stimuli and respond as quickly as possible by depressing the space bar (or other designated key) when and only when the star outline is perceived preceding the solid star. If the star outline presentation is too brief to be detected by the subject, step 146 in FIG. 3(b) slows down (increases) the stimulus presentation time. On the other hand, when a predetermined number of consecutive elections (e.g., 3) are made without error, step 120 shortens the stimulus display time.

Note that at step 112, the initial inspection time is set based on the subject's past performance.

At step 128 is FIG. 3(b), a DRS function is implemented. The DRS deterministic random selection) function is a function by which the outcome of the total number of trials will always match a particular probability distribution profile, although any individual outcome is unpredictable. The function accomplishes this by taking past history into account when making a random yes/no decision. The function may be expressed in informal pseudo-code as follows:

TABLE I

```
function DRS (yes_chance, total, yes_already, no already)
// yes_chance probability of YES response (between 0 and 1)
// total total number of responses in set
// yes_already YES responses previously returned
// no_already NO responses previously returned
n = (total * yes chance - yes already)/(total - yes_already - no_already)
rnd = random 0 // random number less than 1 but greater
than or equal to zero
if n > rnd then
    return (YES)
else
    return (NO)
end if
end function
```

The DRS function is used in many of the tests conducted herein. In step 128, it s set to select the "Display Outline" path with a probability of 0.6.

PERCEPTUAL AWARENESS THRESHOLD TEST

Figures 1, 5:
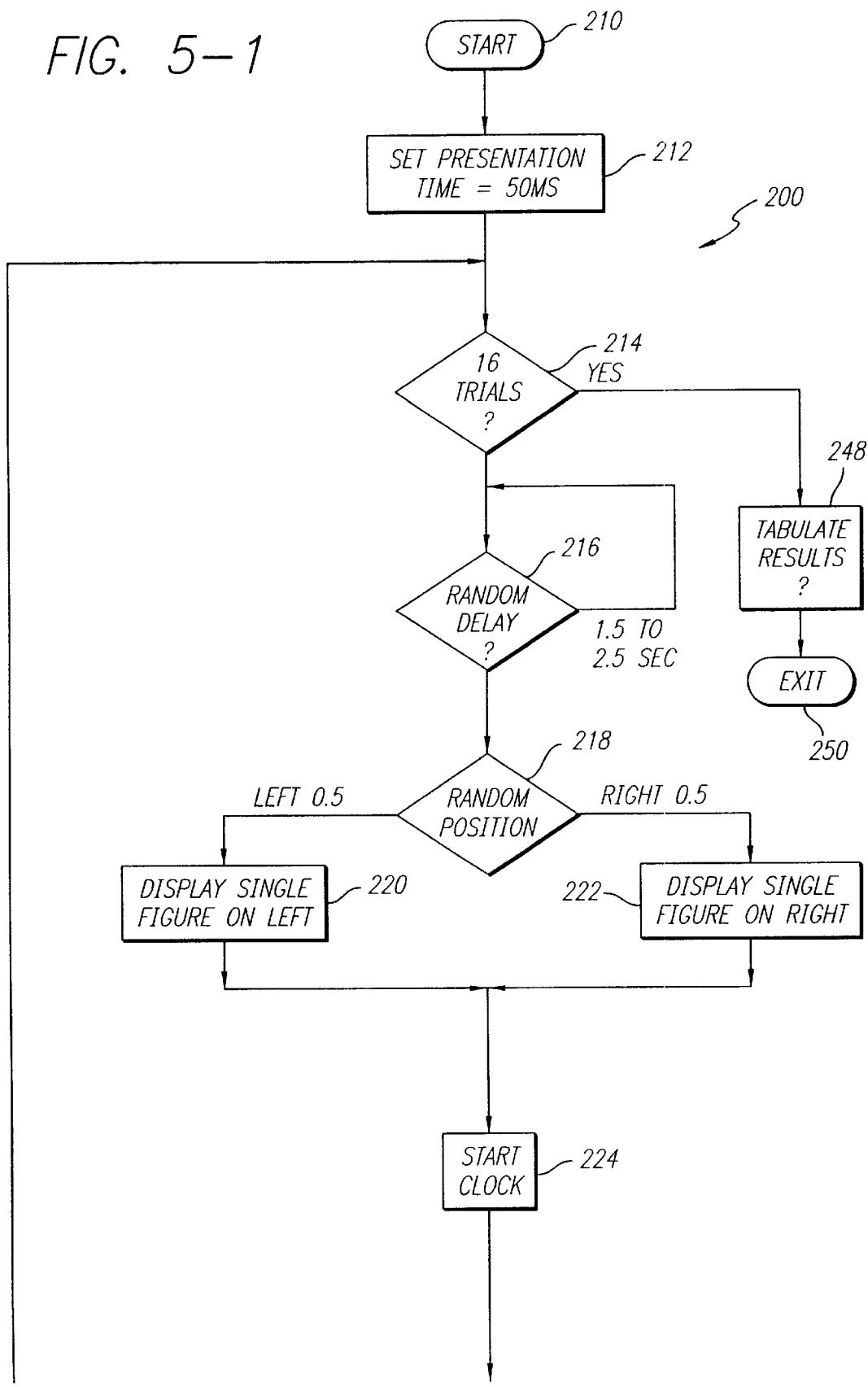
FIG. 5 depicts a flow diagram of a routine which administers a perceptual awareness threshold test in accordance with the teachings of the present invention.
Figures 2, 5:
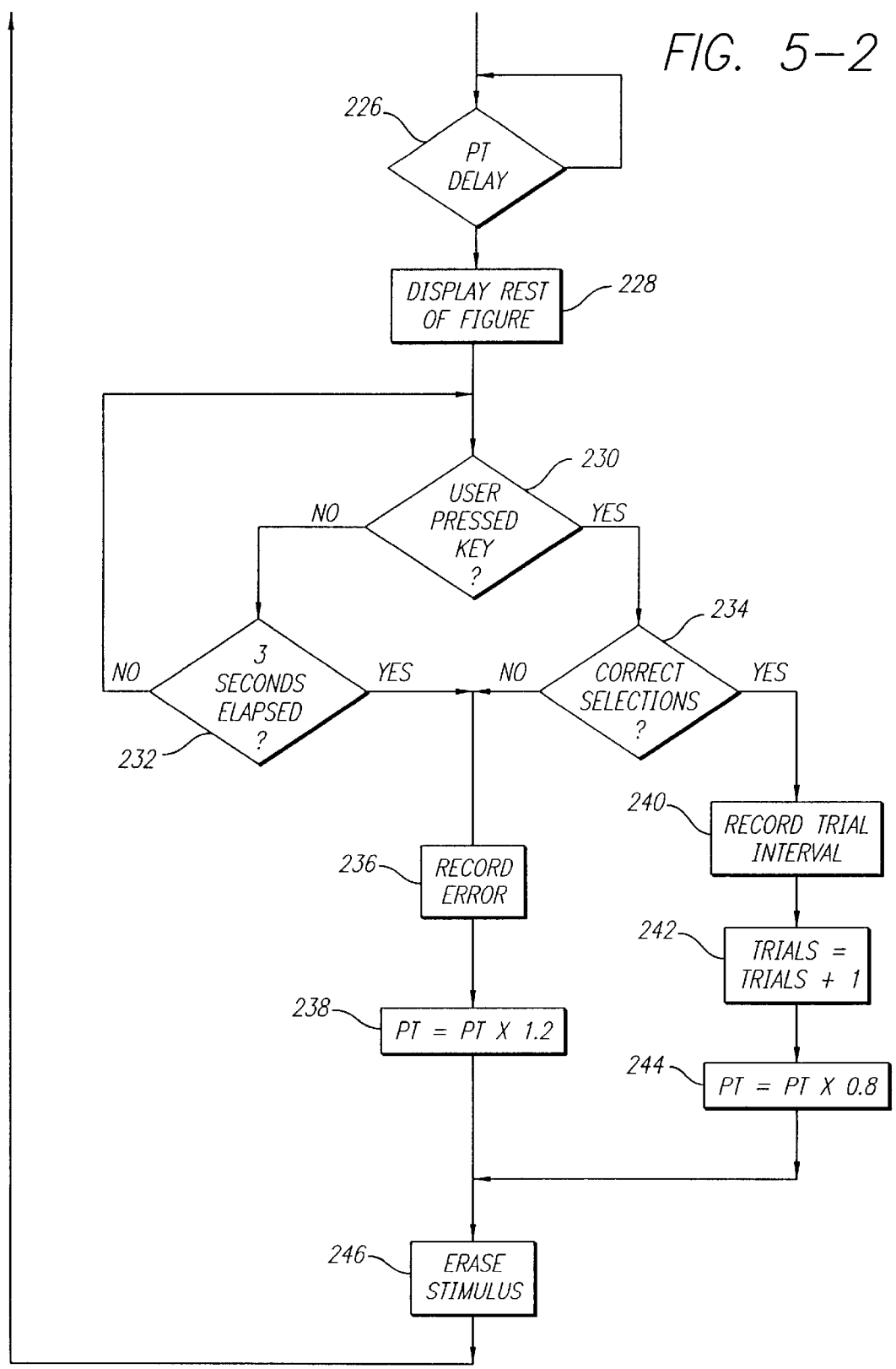
FIG. 2 is a test figure such as that utilized by the system of the present invention for testing reaction time.

FIG. 5 depicts a flow diagram of a routine which administers a perceptual awareness threshold test in accordance with the teachings of the present invention.

Figure 6:
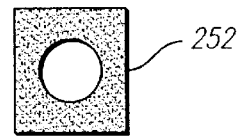
FIG. 6 illustrates an individual figure utilized during the perceptual awareness threshold test.

FIG. 6 illustrates an individual figure utilized during the perceptual awareness threshold test.

Figure 7:
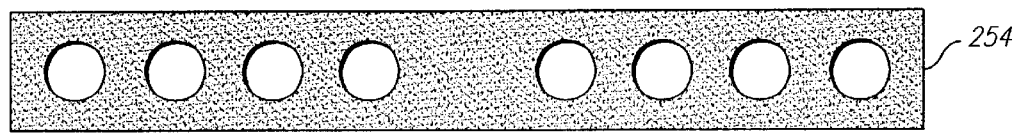
FIG. 7 illustrates a second display figure utilized during the perceptual awareness threshold test.

FIG. 7 illustrates a second display figure utilized during the perceptual awareness threshold test. During this test, the system first adjusts the presentation time based on the object's past performance (step 212). At steps 218–222 in FIG. 5, during the perceptual awareness threshold test, an individual figure, such as that shown in FIG. 6, is presented on a black background in the same position as one of the circles on the left or right side of the displayed figure. After a presentation delay which is determined in part by the subject's past performance (e.g., 20 to 50 milliseconds), the rest of the figure FIG. 7) is displayed. To the subject, the screen appears to contain 8 lights, one of which turns on a little before the rest.

The subject presses one of two keys to indicate on which side, left or right, the initial single figure was displayed (e.g., the right-arrow key if the single figure speared on the right, or the left-arrow key if the figure appeared on the left). If the subject selected the correct side, the presentation delay is reduced (step 244); if the subject selected the wrong side or failed to respond within 3 seconds of the presentation of the stimulus, the presentation delay is increased (step 238). Trial errors and response times are recorded for tabulation at the end of the test.

MULTIPLE-CHOICE REACTION TIME TEST

Figures 2, 8:
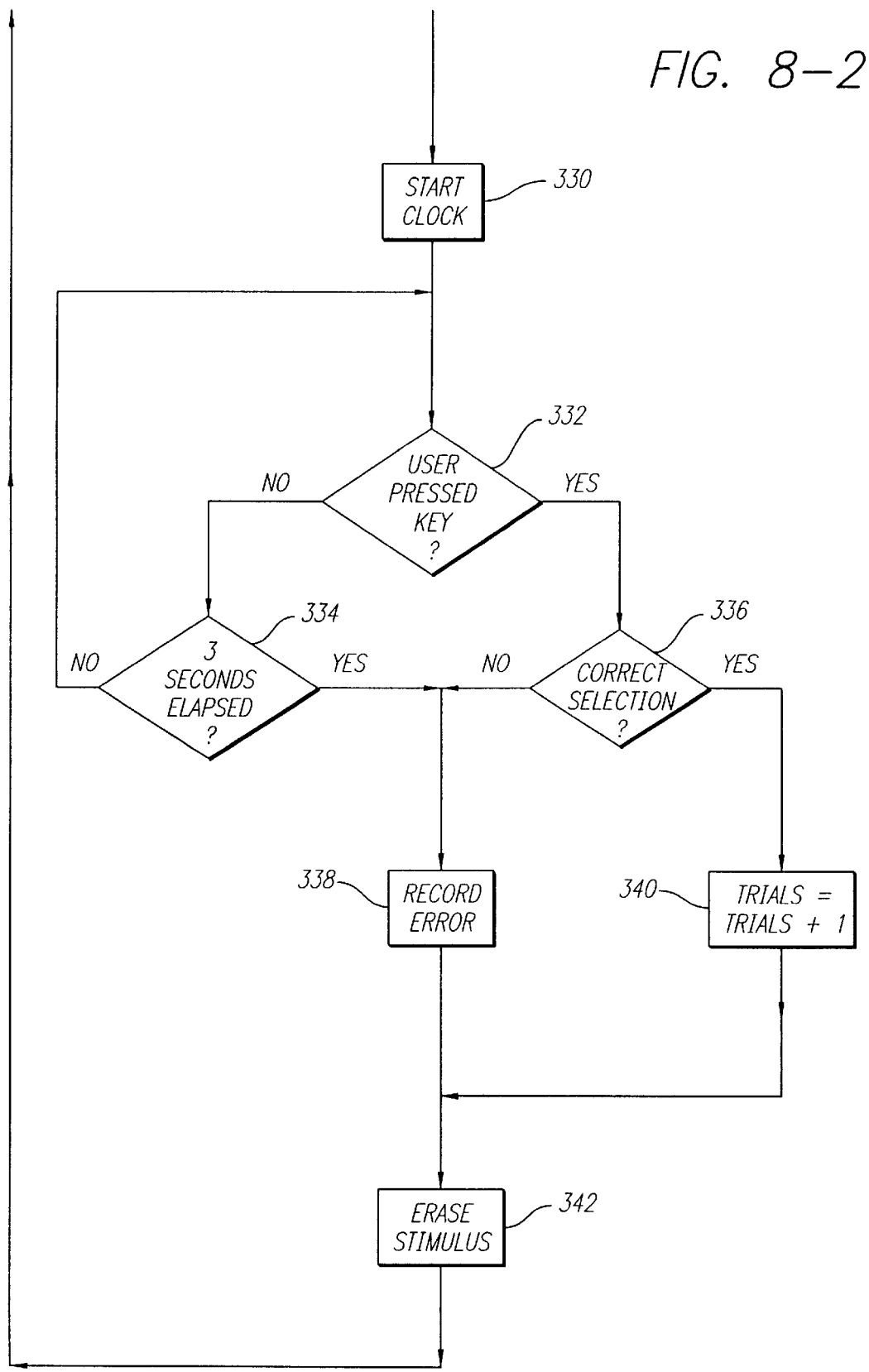
FIG. 8 depicts a flow diagram of a routine which administers a multiple choice reaction time test in accordance with the teachings of the present invention.

FIG. 8 depicts a flow diagram of a routine which administers a multiple-choice reaction time test in accordance with the teachings of the present invention. The display of FIG. 9 is used.

Figure 9:
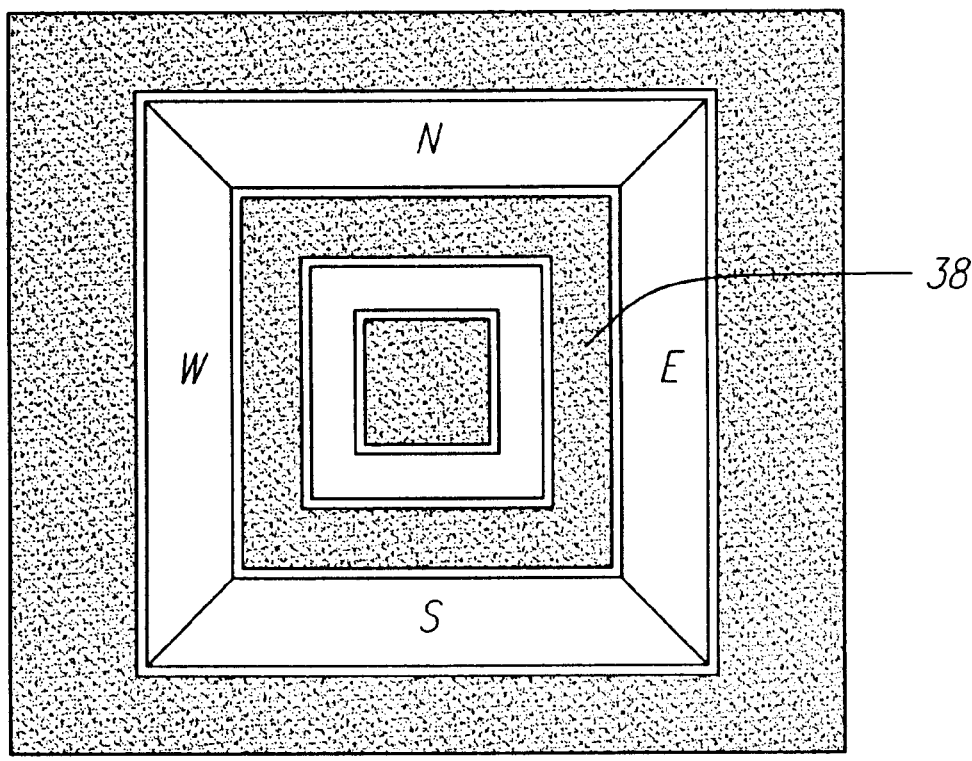
FIG. 9 is a display figure utilized during the multiple-choice reaction time test.

FIG. 9 is a display figure utilized during the multiple-choice reaction time test. During this test, the segments labeled N, S, E, and W normally form dark red square ring. The stimulus consists of one of these segments changing to a light yellow color. At the same time, the moat 38 may or may not change color from ark blue to light cyan. The subject responds by depressing the appropriate key. If the moat is illuminated (i.e., has changed color), the subject must also press the shift key the responses are tabulated for subsequent display.

WORKING MEMORY CAPACITY TEST

Figures 1, 10:
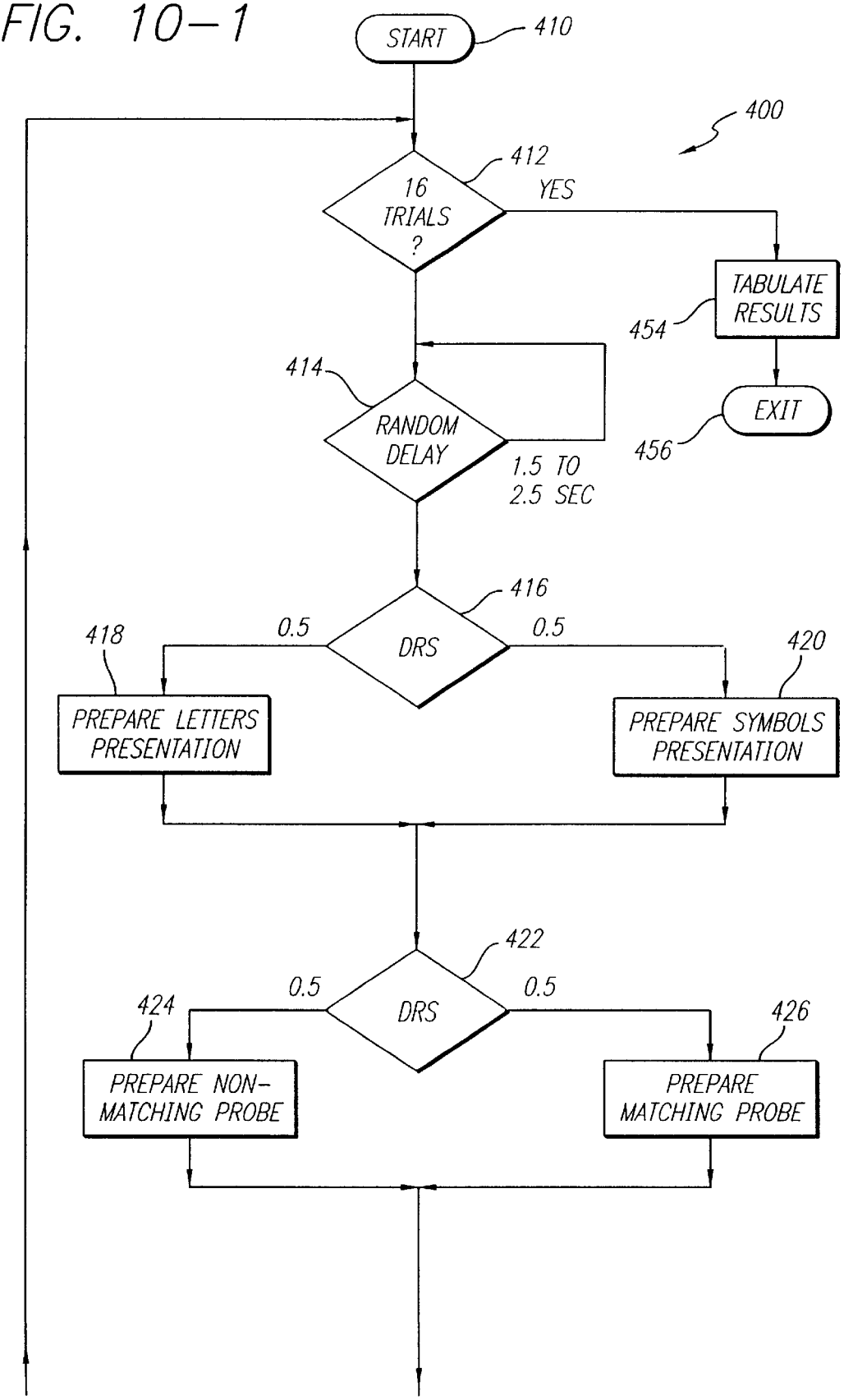
FIG. 10 depicts a flow diagram of a routine which administers a short term memory test in accordance with the teachings of the present invention.
Figures 2, 10:
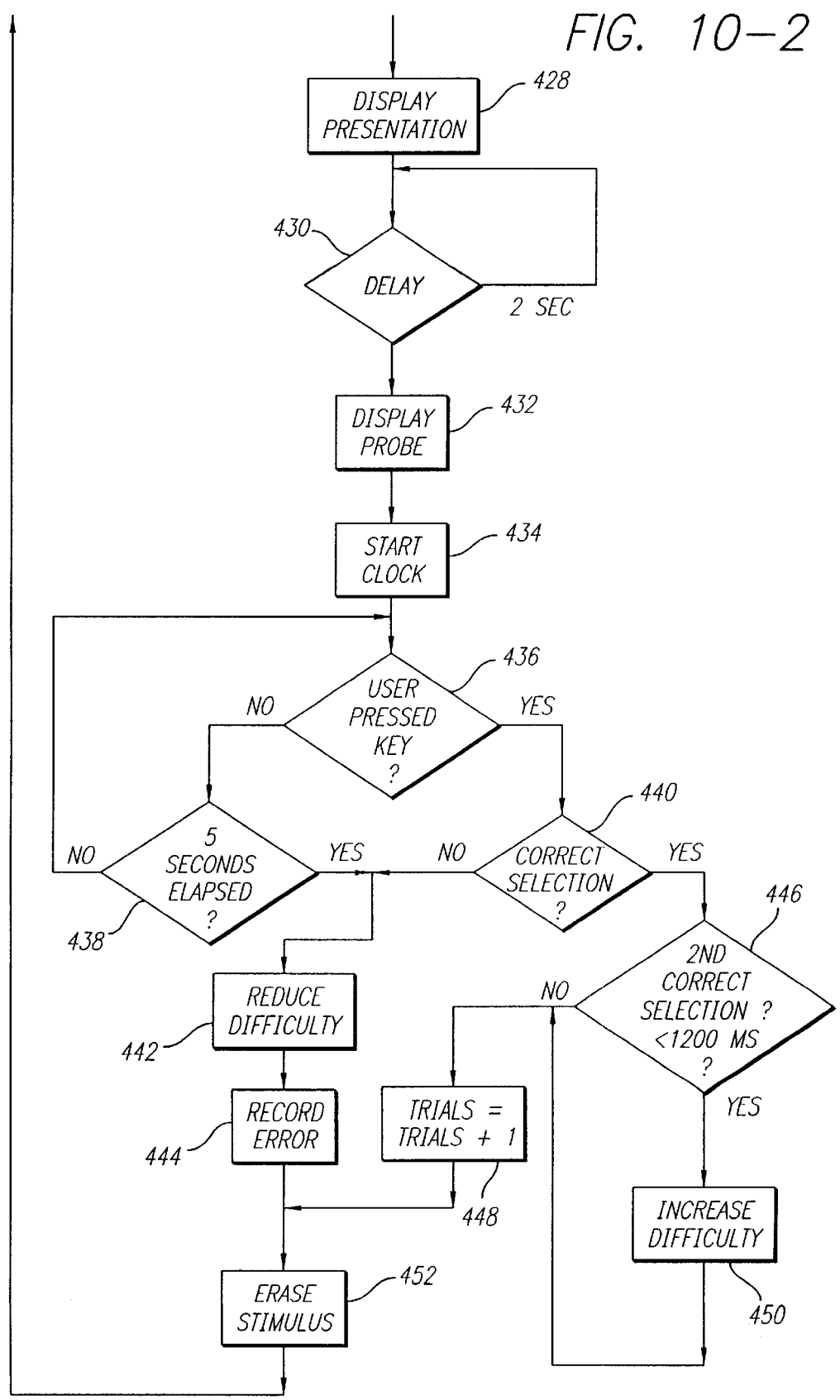

FIG. 10 depicts a flow diagram of a routine which administers a working memory capacity test in accordance with the teachings of the present invention. In this test 400, after a random delay, the system performs a DRS function to select a "letters" or "symbols" test with equal probability. The two forms of the test are identical, except that one displays a set of capital letters A–Z, and the other a set of geometrical symbols (circle, triangle, and square) with any of three concentric segments filled-in or empty, as illustrated in FIG. 11(a) and (b). FIG. 11(a) and (b) depict display figures utilized by the short term memory test.

In step 428, an initial set of characters is displayed (the "presentations"). The number of letters or symbols presented is determined by past performance, and ranges between 3 and 13. The letters or symbols are presented in random order, and are all different from one another.

After a short delay (step 430), the presentation is erased and a "probe" of a smaller number of characters is displayed. The probe consists of a random set of letters or symbols, and may or may not (with 50% likelihood) contain one or more letters or symbols that also appeared in the presentation. The count of probe characters ranges from 1 to 11.

If the probe contains a letter or symbol that appeared in the presentation, the subject is to press a YES key (e.g., the right-arrow key); if none of the probe characters were part of the presentation, the subject is to press a NO key (e.g., the left arrow key).

If the subject responded incorrectly, the number of letters or symbols is reduced or the next letters or symbols trial. If the subject responds correctly to two consecutive trials without an intervening error and with a reaction time of less than 1200 milliseconds, the number of letters or symbols is increased for the next trial (step 450).

A score representing the aggregate difficulty of the test is obtained by summing the total characters (letters and symbols) correctly identified during the test run of 8 letter trials and 8 symbol trials.

WORD PICTURE ASSOCIATION TEST

Figures 2, 12:
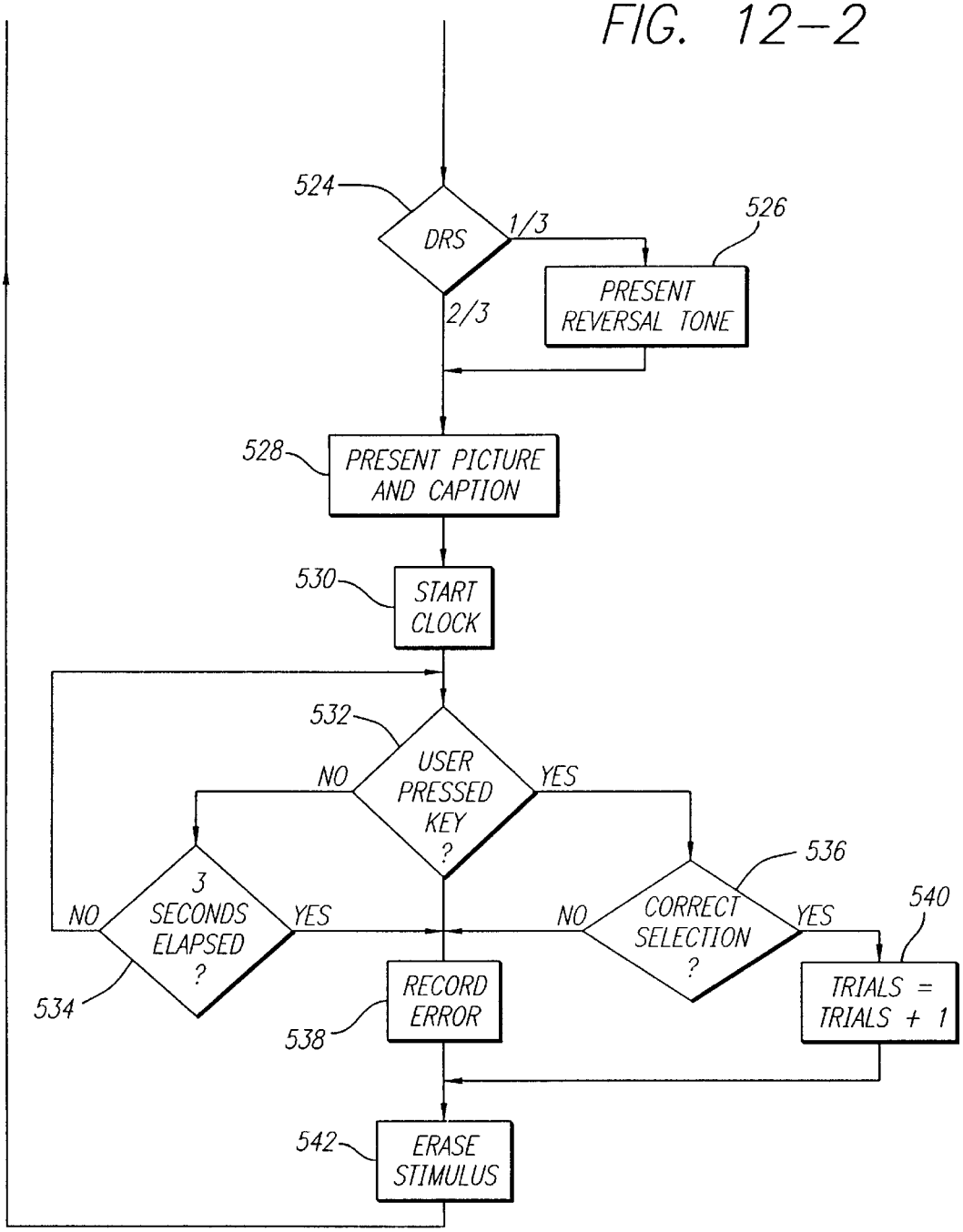
FIG. 12 depicts a flow diagram of a routine which administers a word picture association test in accordance with the teachings of the present invention.

FIG. 12 depicts a flow diagram of a routine which administers a word picture association test in accordance with the teachings of the present invention. During this test, a word is presented along with a picture. If they are the same, the subject is instructed to respond with a YES indication. If not, the subject responds with a NO. However, if a tone sounds during the trial, the subject is to reverse his answer only for that trial.

DATA ANALYSIS

The reaction time (RT) and other test-specific data (e.g., inspection time, presentation time, character count) are analyzed statistically for each test to produce the following results (in all cases the fastest, slowest, and any erroneous trials are excluded from the RT computation):

Physical reaction time (milliseconds): computed as the median RT in the Reaction Time Test.

Subliminal awareness threshold (milliseconds): computed as the briefest interval successfully observed by the subject during a "set" of 5 trials in the Subliminal awareness Threshold Test (FIG. 3(*a*)).

Perceptual awareness threshold (milliseconds): computed as the briefest presentation delay successfully observed by the subject in 3 successive trials in the Perceptual awareness Threshold Test (FIG. 5).

Information processing/Decision making speed (milliseconds): computed as the median ~T in the Multiple Choice Reaction Time Test (FIG. 8).

Efficiency: for a given test, a percentage computed according to the formula $$\text{Efficiency} = 100N(RT-S)/RT(N+ERR)$$

where N is the number of trials after the fastest and slowest trials are discarded, and does not include erroneous trials; RT is the median reaction time in milliseconds for correctly completed trials; S is the standard deviation (sigma) of the RTs, a measurement of "noise" in the cognitive system (the standard deviation is computed by averaging the squares of the difference of the RT of each trial and the mean RT, then taking the square root of the average); ERR is the number of incorrect trials. A test completed with all RTs exactly the same would yield an efficiency of 100%. Efficiency measures the consistency, rather than the speed, of the subject's reactions. Typical efficiencies range from 75% to 90%; more complex tests tend to produce lower efficiency figures for a given subject. Research has indicated that intra-individual variability in RT, which the Efficiency level reflects, is highly correlated with g Jensen 1982].

Working memory capacity: computed as the total number of characters displayed in the presentation and probe sets of the Working memory Capacity Test (FIG. 10) in those trials that are successfully completed by the subject. This can range from 64 (3 presentation and 1 probe characters in 16 trials) to 384 (13 presentation and 11 probe characters in 16 trials).

Performance level (PL): a conveniently-scaled "score" used to give the subject a relative idea of his performance. The performance level is computed in two stages, first a get an "adjusted RT" reflecting efficiency $$RTadj = 100RT/\text{Efficiency}$$

then the actual performance level is scaled from RTadj such that PL=50 for a subject in the 20th percentile of performance, and PL=100 for a subject in the 90th percentile of performance. The scale factor used varies with the particular test, as more complex tests result in larger RTs.

DATA RECORDING AND DISPLAY

Detailed information about each trial, consisting of RT and perceptual threshold or difficulty level as appropriate, is available for display upon completion of the test. The subject can see, for example, the effect of the appearance of letters or symbols in the Working memory Capacity test, or the difference in response times for individual trials in the Word-Picture Test when the reversing tone is present. This per-trial information is then discarded, and only summary results are saved.

The subject may enter a comment at the completion of any test to describe any factors that he thinks may have influenced his score. This comment will appear on the history graph described below whenever the period of time including the comment is displayed.

The summary test results described above are time and date-stamped and saved for subsequent review. The system provides a History graph, on which may be selected for display any of the above results for any period of time. This History information, coupled with the comment entry described above, allows the subject to track his performance over time and identify what factors influence his performance. In addition, he user may view results from multiple tests plotted with their results averaged together, to see the effect of a combination of tests. Specific starting and ending dates may be selected.

The History graph may be operated in either of two modes. In TEMPORAL node, performance history is displayed over time, with date/time labels on the X-axis. Each type of data is plotted as a line graph. In PERIODIC mode, the data can be examined for cyclic behavior. In addition to starting and ending dates, the user selects he number of days in the period. All the data between starting and ending dates is scatter-plotted (each data value is plotted as a point on the graph) in segments of the specified number of days. For example, the performance of the subject for various times of the day could be displayed by setting the period to 1 day. All the 8:00 a.m. results for the entire history period will be plotted next to each other, all the 9:00 a.m. results likewise, and so on. Similarly, a weekly cycle could be displayed by setting the period to 7 days. If the starting date is set to a Sunday, then Day 0 on the graph will hold all the Sunday scores, day 1 will hold all the Monday scores, etc.

Thus, the present invention has been described herein with reference to a particular embodiment for a particular application. Those having ordinary skill in the art and access to the present teachings will recognize additional modifications applications and embodiments within the scope thereof. For example, the invention is not limited to the particular tests disclosed. Other tests may be incorporated as will be appreciated by those skilled in the art.

It is therefore intended by the appended claims to cover any and all such applications, modifications and embodiments within the scope of the present invention.

Accordingly, what is claimed is:

1. An interactive automatic system for measuring and analyzing mental ability including:

first means for automatically providing a stimulus for a duration of time;

second means for automatically measuring a subject's reaction to said stimulus and providing data in response thereto, said second means including means for measuring said subject's physical reaction time;

third means responsive to said second means for adjusting the duration of time during which the stimulus is provided by the first means in response to said data; and fourth means responsive to said means for measuring said subject's physical reaction time for measuring the subject's threshold of perceptual discrimination.

2. The invention of claim 1 including means for measuring the subject's perceptual awareness thresholds.

3. The invention of claim 1 including means for measuring the subject's brain processing speed and efficiency.

4. The invention of claim 1 including means for measuring the subject's cognitive capacity (speed, efficiency and capacity) for information processing.

5. The invention of claim 1 including means for measuring the subject's cognitive capacity (speed, efficiency and capacity) for choice, descrimination and decision responses.

6. The invention of claim 1 including means for measuring the subject's cognitive capacity (speed, efficiency and capacity) of accessing various areas of short and long term memory.

7. The invention of claim 1 including means for interactive adjustment of test complexity based on said measurements.

8. The invention of claim 1 including means for quantifying the information exchange rate between the subject's left and right brain hemispheres.

9. The invention of claim 1 including means for non-invasive identification and quantification of neural noise in the brain and elementary cognitive processing pathways.

10. The invention of claim 1 including means for measuring the subject's level of attention.

11. The invention of claim 1 including means for compiling a history of the data, providing specific comments in response to said data, and granting a level's rating for the subject's overall mental and physical performance.

12. An interactive automatic method for measuring and analyzing mental ability including the steps of:

automatically presenting an auditory or visual stimulus for a period of time, automatically measuring a physical reaction to said stimulus, and adjusting the period of time during which the stimulus is presented in response to the measured physical reaction time to ascertain a subject's threshold of perceptual discrimination.

13. The invention of claim 12 including the step of measuring perceptual awareness thresholds.

14. The invention of claim 12 including the step of measuring the subject's brain processing speed and efficiency.

15. The invention of claim 12 including the step of measuring the subject's cognitive capacity (speed, efficiency and capacity) for information processing.

16. The invention of claim 12 including the step of measuring the subject's cognitive capacity (speed, efficiency and capacity) for rendering choice discrimination and decision responses.

17. The invention of claim 12 including the step of measuring the subject's cognitive capacity for accessing various areas of short and long term memory.

18. The invention of claim 12 including the step of interactive adjustment of test complexity based on said measurements.

19. The invention of claim 12 including the step of quantifying the information exchange rate between the subject's left and right brain hemispheres.

20. The invention of claim 12 including the step of non invasive identification and quantification of neural noise in the brain and elementary cognitive processing pathways.

21. The invention of claim 12 including the step of measuring the subject's level of attention.

22. The invention of claim 12 including the steps of repeating the steps of claim 13 to compile a history of scores, provide specific comments in response to said scores, and grant a level's rating for the subject's overall mental and physical performance.

23. An interactive automatic system for measuring and analyzing mental ability including:

first means for automatically providing a primary stimulus;

second means for randomly providing a second, rule-altering stimulus simultaneously with the primary stimulus;

third means for automatically measuring a subject's reaction to said stimuli and providing data in response thereto;

fourth means responsive to said third means for outputting said data.

24. An interactive automatic system for measuring and analyzing mental ability via a battery of cognitive tasks including:

first means for automatically providing a diversity of stimulus elements for a duration of time including random audio and visual content including lights, sounds, letters, words, pictures and/or symbols;

second means for automatically measuring a subject's reaction to said stimuli and providing data in response thereto;

third means for adjusting the stimuli of first means in response to said data; and fourth means for outputting said data.

25. An interactive automatic system for measuring and analyzing mental ability including:

first means for automatically providing a stimulus for a duration of time;

second means for automatically measuring a subject's reaction to said stimulus and providing data in response thereto, said second means including means for measuring said subject's reaction time; and third means responsive to said second means for adjusting the duration of time during which the stimulus is provided by the first means in response to said data until the duration of stimuli presentation is substantially equal to the subject's threshold of perceptual discrimination.

* * * * *